United States Patent
Taniguchi et al.

(10) Patent No.: US 9,283,122 B2
(45) Date of Patent: Mar. 15, 2016

(54) TAMPON APPLICATOR

(75) Inventors: Kenta Taniguchi, Kagawa (JP); Yukihiro Ito, Kagawa (JP); Kouichi Yamaki, Kagawa (JP)

(73) Assignee: UNICHARM CORPORATION, Ehime-Ken (JP)

( * ) Notice: Subject to any disclaimer, the term of this patent is extended or adjusted under 35 U.S.C. 154(b) by 114 days.

(21) Appl. No.: 14/002,233

(22) PCT Filed: Feb. 28, 2012

(86) PCT No.: PCT/JP2012/054942
§ 371 (c)(1),
(2), (4) Date: Nov. 4, 2013

(87) PCT Pub. No.: WO2012/118080
PCT Pub. Date: Sep. 7, 2012

(65) Prior Publication Data
US 2014/0046239 A1    Feb. 13, 2014

(30) Foreign Application Priority Data
Mar. 1, 2011   (JP) .................................. 2011-044144

(51) Int. Cl.
*A61F 13/32*   (2006.01)
*A61F 13/26*   (2006.01)
*A61F 13/20*   (2006.01)

(52) U.S. Cl.
CPC ........... *A61F 13/266* (2013.01); *A61F 13/2077* (2013.01); *A61F 13/26* (2013.01)

(58) Field of Classification Search
CPC .... A61F 13/2077; A61F 13/26; A61F 13/266
See application file for complete search history.

(56) References Cited

U.S. PATENT DOCUMENTS

| 5,135,475 | A | 8/1992 | Nakanishi et al. | |
|---|---|---|---|---|
| 2003/0163080 | A1 | 8/2003 | Lemay et al. | |
| 2004/0010220 | A1* | 1/2004 | Miller et al. | 604/15 |
| 2005/0070839 | A1* | 3/2005 | Jackson et al. | 604/11 |
| 2006/0025742 | A1 | 2/2006 | Hasse et al. | |
| 2007/0156080 | A1* | 7/2007 | Loyd et al. | 604/15 |
| 2008/0033337 | A1* | 2/2008 | Dougherty et al. | 604/15 |
| 2008/0167598 | A1* | 7/2008 | Gann et al. | 604/14 |
| 2008/0167599 | A1* | 7/2008 | Osborn et al. | 604/14 |

(Continued)

FOREIGN PATENT DOCUMENTS

| JP | 2-246973 A | 10/1990 |
|---|---|---|
| JP | 8-117283 A | 5/1996 |

(Continued)

OTHER PUBLICATIONS

International Search Report and Written Opinion corresponding to PCT/JP2012/054942, dated May 29, 2012.

(Continued)

*Primary Examiner* — Susan Su
(74) *Attorney, Agent, or Firm* — Hauptman Ham, LLP

(57) ABSTRACT

A tampon applicator includes an outer cylinder having an absorbent; an inner cylinder configured to push the absorbent into the outer cylinder; and a flange part extending outward in a radial direction from an outer peripheral surface of a grip cylinder part of the outer cylinder. The flange part is provided with a flange identifying unit including at least one of an identifying display portion; an identifying friction portion; or an identifying shape portion.

5 Claims, 4 Drawing Sheets

(56) References Cited

U.S. PATENT DOCUMENTS

| | | | |
|---|---|---|---|
| 2008/0228128 A1* | 9/2008 | Karapasha et al. | 604/15 |
| 2008/0255496 A1 | 10/2008 | Sargent et al. | |
| 2009/0247815 A1* | 10/2009 | Hou et al. | 600/29 |
| 2009/0247928 A1 | 10/2009 | Bartning et al. | |
| 2009/0247929 A1* | 10/2009 | Hou et al. | 604/15 |
| 2010/0016780 A1 | 1/2010 | Vandenbogart et al. | |
| 2010/0197997 A1 | 8/2010 | Hou et al. | |
| 2011/0105830 A1* | 5/2011 | Hou et al. | 600/30 |
| 2011/0144561 A1* | 6/2011 | Watanabe et al. | 604/15 |
| 2011/0152742 A1* | 6/2011 | Winkel et al. | 604/15 |
| 2012/0071839 A1* | 3/2012 | Wada et al. | 604/286 |
| 2013/0237898 A1* | 9/2013 | Kirkham et al. | 604/15 |
| 2013/0331763 A1* | 12/2013 | Ito et al. | 604/11 |
| 2014/0052048 A1* | 2/2014 | Taniguchi et al. | 604/15 |
| 2014/0155809 A1* | 6/2014 | Taniguchi et al. | 604/15 |

FOREIGN PATENT DOCUMENTS

| | | |
|---|---|---|
| JP | 2009-240784 A | 10/2009 |
| JP | 2009-240785 A | 10/2009 |
| JP | 2009-240786 A | 10/2009 |
| JP | 2010-057927 A | 3/2010 |

OTHER PUBLICATIONS

Extended European Search Report issued Oct. 17, 2014, corresponding to European patent application No. 12752386.8.

Office Action mailed Feb. 3, 2015, corresponding to Japanese patent application No. 2011-044144.

Office Action mailed Apr. 21, 2015, corresponding to Japanese patent application No. 2011-044144.

Office Action dated Sep. 7, 2015, corresponding to European Patent Application No. 12752386.8.

* cited by examiner

TAMPON APPLICATOR

RELATED APPLICATIONS

The present application is a National Phase of International Application Number PCT/JP2012/054942, filed Feb. 28, 2012, and claims priority from Japanese Application Number 2011-044144, filed Mar. 1, 2011.

TECHNICAL FIELD

The present invention relates to a tampon applicator.

BACKGROUND ART

Conventionally, a sanitary tampon with an applicator is provided. A tampon applicator includes an outer tube and an inner tube. An absorber having a withdrawal string is contained inside the outer tube. When using a sanitary tampon, a user inserts the outer tube inside the vagina while holding the outer tube and then presses the inner tube toward the outer tube. When the inner tube is pressed toward the outer tube, the absorber is pushed out from the outer tube and is arranged inside the vagina. However, when using a sanitary tampon, if the user pushes out the absorber when the outer tube has not been inserted up to an appropriate depth, the absorber is not arranged at an appropriate position inside the vagina.

Patent Literature 1 describes a tampon applicator that has been made in view of this problem. The tampon applicator includes a curved-shaped collar portion extending out towards the circumference of the outer tube. When using the sanitary tampon, the user presses the outer tube via the collar portion, and inserts the outer tube inside the vagina. When the outer tube is inserted up to an appropriate depth, the collar portion comes in contact with the vaginal opening. Therefore, the user can insert the outer tube up to the appropriate depth. When the user pushes out the absorber with the outer tube inserted up to an appropriate depth, the absorber is arranged at an appropriate position inside the vagina.

CITATION LIST

Patent Literature

[Patent Literature 1] Publication of Japanese Patent No. 3217617

SUMMARY OF INVENTION

However, the applicants discovered the following problem in the aforementioned tampon applicator.

There is a user who cannot clearly discriminate between the outer tube and the collar portion at the time of using the tampon because the toilets, etc., where a tampon is used, are relatively dark, and therefore, it may not be possible for the user to clearly understand if the collar portion is in contact with the vaginal opening. Furthermore, there is another user who inserts the tampon inside the vagina with opening the genital labia with one hand and holding the tampon in the other hand. The user cannot directly have a visual contact with the tampon by the working hand, and therefore, it may not be possible for the user to clearly understand whether the collar portion is in contact with the vaginal opening. That is, it may not be possible for the user to visually know if the collar portion is in contact with the vaginal opening.

When the user cannot clearly and visually understand whether the collar portion is in contact with the vaginal opening, the user can know that the collar portion is in contact with the vaginal opening by a feeling of the area near the vaginal opening. However, for example, if a portion other than the collar portion of the tampon applicator and the finger, etc., of the user are in contact with the vaginal opening, it may be wrongly perceived that the collar portion is in contact with the vaginal opening. If the user pushes out the absorber inside the vagina while the collar portion is not in contact with the vaginal opening, the absorber may not be arranged at an appropriate position inside the vagina.

Therefore, the present invention has been achieved in view of the aforementioned problems, and an object thereof is to provide a tampon applicator with which it is possible to easily arrange an absorber at an appropriate position inside the vagina.

To solve the above problem, a tampon applicator (tampon applicator 1) according to the present invention comprises: an outer tube (outer tube 2) that contains an absorber (absorber 4) therein and that is provided with a push-out opening (push-out opening 8) at one side from which the absorber is pushed out and a grip tube portion (grip tube portion 7) at the other side; an inner tube (inner tube 3) that is inserted into the grip tube portion and is able to push out the absorber outward from the push-out opening by the movement into the outer tube, and a collar portion (collar portion 11) extended from an outer circumference surface of the grip tube portion of the outer tube towards outer side in a radial direction, and wherein the collar portion is provided with a collar distinguishable portion including at least any one of a distinguishable display portion (distinguishable display portion 11b, 12b, 14b) having a color or a pattern different from at least either one of the outer tube and the inner tube, a distinguishable friction portion (distinguishable friction portion 12c) having a friction coefficient different from the friction coefficient of the surface of at least either one of the outer tube and the inner tube, and a distinguishable shape portion (distinguishable shape portion 13d, 14d) having an outer peripheral shape different from at least either one of the outer tube and the inner tube.

DESCRIPTION OF EMBODIMENTS

First Embodiment

Figure 1:
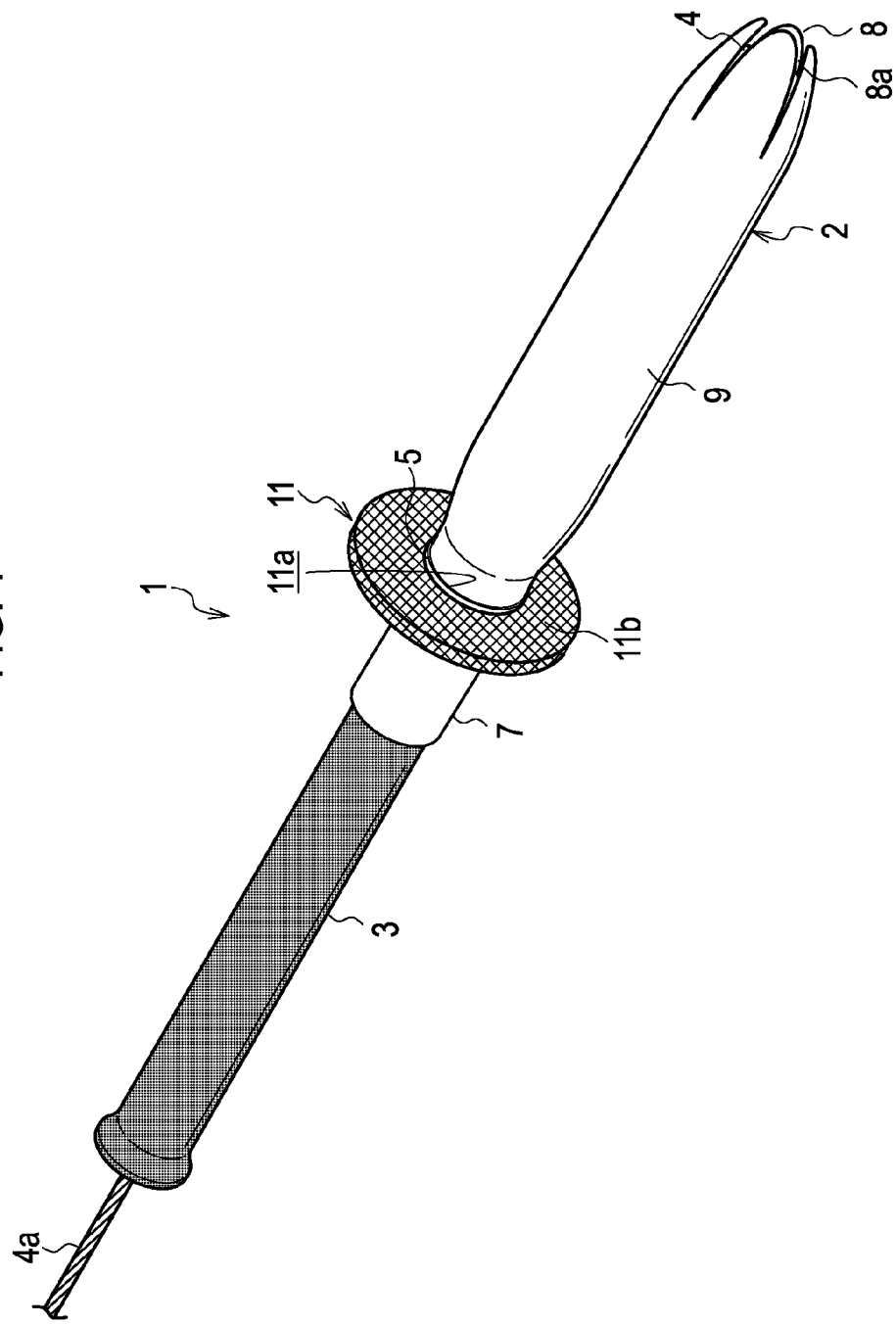
FIG. 1 is a perspective view of a tampon applicator according to a first embodiment of the present invention.
Figure 2:
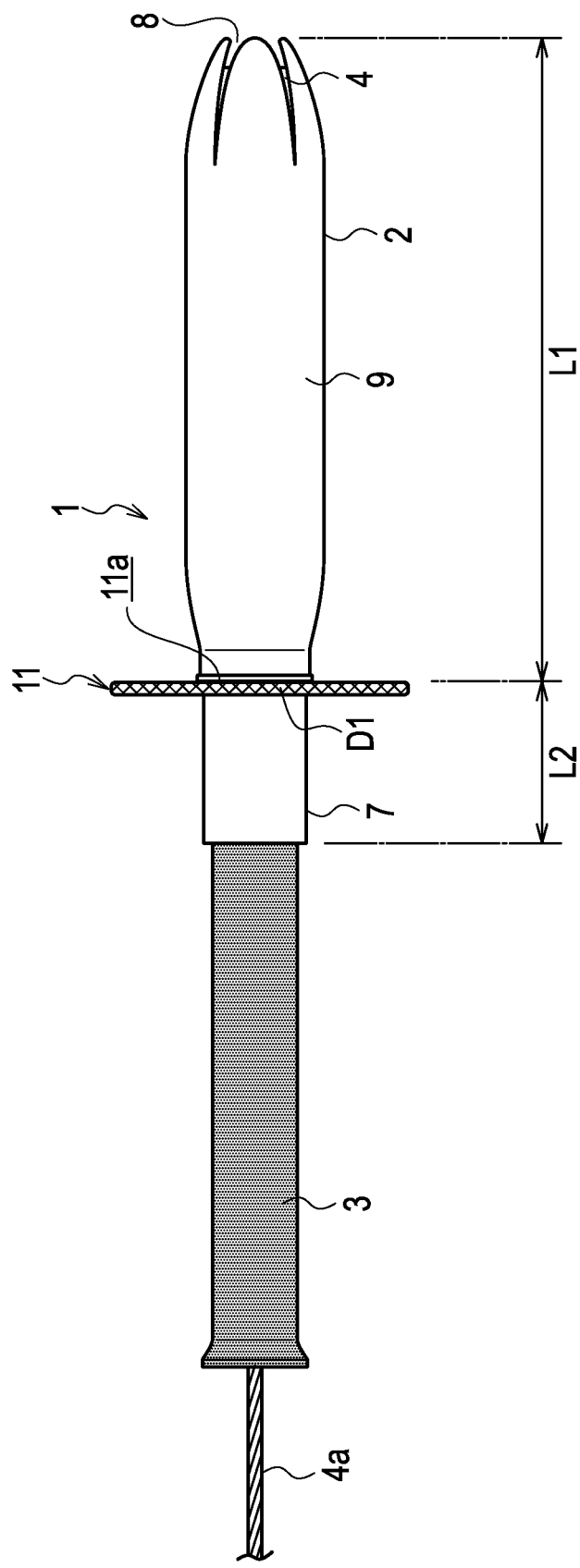
FIG. 2 is a plan view of the tampon applicator shown in FIG. 1.

With reference to FIG. 1 and FIG. 2, a tampon applicator according to a first embodiment of the present invention will be explained. FIG. 1 is a perspective view showing the entire tampon applicator according to the first embodiment, and FIG. 2 is a plan view of the tampon applicator shown in FIG. 1.

A tampon applicator 1 has an outer tube 2 and an inner tube 3. The outer tube 2 and the inner tube 3 are cylindrical in shape having a hollow portion therein. The cross-sectional shape of the outer tube 2 and the inner tube 3 is a perfect circle. The outer tube 2 and the inner tube 3 are entirely formed by a polyolefin resin such as polyethylene and polypropylene, or by a cardboard whose surface is laminated with a polyolefin film.

In the present embodiment, the outer tube 2 and the inner tube 3 are formed, through mold injection, by mixing together polyethylene and polypropylene, 1% or more of a pigment, and 1% or more of a lubricant. The inner tube 3 includes a pigment different from the outer tube 2, and is colored differently from the outer tube 2. Although the cross-sectional shape of the outer tube 2 and the inner tube 3 according to the present embodiment is a perfect circle, the cross-sectional shape of the outer tube 2 and the inner tube 3 according to the present invention may be any shape, for example, an elliptical shape, as long as the inner tube and the outer tube may be easily inserted into the vagina.

An absorber 4 is contained inside the outer tube 2 as a tampon. A withdrawal string 4a is connected to the absorber 4. The withdrawal string 4a is inserted inside the inner tube 3 from an end of the absorber 4, and the inserted end is extracted out from the inner tube 3. By pulling the withdrawal string 4a during use, the absorber 4 can be pulled out from inside the body.

A push-out opening 8 from which the absorber 4 is pushed out is formed at an end of the outer tube 2. A petal body 8a that is deformed towards the radially outer side when the absorber 4 is pushed out is formed in the push-out opening 8. The petal body 8a is constantly closed at an edge of the push-out opening 8, but is flared by the absorber 4 to be opened up when the absorber 4 is pushed out by the inner tube 3. Thus, the absorber 4 is pushed out from the outer tube 2, and can be inserted inside the user's body.

At the other end of the outer tube 2, a grip tube portion 7 held by fingers during the moving operation of the outer tube 2 and the inner tube 3 is provided. The grip tube portion 7 has a diameter smaller than a diameter of an outer tube main body 9 between the push-out opening 8 and the grip tube portion 7. A distal end of the inner tube 3 is inserted into the grip tube portion 7, and the inserted distal end surface of the inner tube 3 faces the absorber 4. An end of the outer tube main body 9 at the side of the grip tube portion 7 is narrowed to have almost the same diameter as that of the grip tube portion 7, and a protrusion part 5 is formed at the other end thereof. The protrusion part 5 comes in contact with the collar portion 11 to be described below, and restricts the movement of the collar portion 11 so as not to allow The collar portion 11 extending radially outward from the grip tube portion 7 is attached to the grip tube portion 7. The collar portion 11 is in contact with the protrusion portion 5. A hole portion 11a into which the grip tube portion 7 is inserted is formed in the collar portion 11. A diameter of the hole portion 11a may be equal to or greater than a diameter of an outer circumference of the grip tube portion 7. Furthermore, an inner diameter D1 of the hole portion 11a of the collar portion 11 is lesser than an outer diameter of the protrusion portion 5. Accordingly, the collar portion 11 can move in a circumferential direction and an axial direction of the grip tube portion 7. Furthermore, the movement of the collar portion 11 toward the outer tube main body from the protrusion part 5 is restricted by the protrusion part 5.

In the tampon applicator 1 of the present embodiment, the inner diameter D1 of the collar portion 11 is 9.9 mm, and the outer diameter of the outer tube main body 9 is 13.7 mm. Further, the outer diameter of the grip tube portion 7 is 9.4 mm, and the outer diameter of the protrusion part 5 is 10.4 mm. Further, a length L1 (see FIG. 2) between the collar portion and the end of the outer tube 2 at the side of the push-out opening 8 is 50 mm, and a length L2 (see FIG. 2) between a surface at the side of the distal end of the collar portion 11 and the end of the outer tube 2 at the side of the grip tube portion 7 is 10 mm. The length L2 between the surface at the side of the distal end of the collar portion 11 and the end of the outer tube 2 at the side of the grip tube portion 7 is the length of a portion held by fingers of the user during use. Accordingly, in consideration of user's ease of holding, the length L2 is preferably equal to or greater than 10 mm. Further, the thickness of the collar portion 11 is 1.5 mm. It must be noted that the thickness of the collar portion 11 can be appropriately changed, and may be lesser than 1.5 mm or more than 1.5 mm.

The outer shape of the collar portion 11 is circular in a plan view. The collar portion 11 is colored differently from the surface color of the outer tube 2 and the inner tube 3. A collar distinguishable portion of the collar portion 11 is a distinguishable display portion 11b. The entire collar portion 11 is colored. That is, the entire collar portion 11 functions as the distinguishable display portion 11b. The configuration is such that a color difference between the color of the collar portion 11 and the surface color of the outer tube 2 or the inner tube 3 is 7.3 or more.

The collar portion 11 is configured of a polyolefin resin, an elastomer, paper, or any other material. The collar portion 11 according to the present embodiment is formed by injection-molding a polyethylene and polypropylene resin, a pigment, and a lubricant. The pigment is preferably added in a range of 0% to 8% for other materials of the collar portion 11.

It is noted that the collar portion 11 according to the present embodiment is colored by adding pigment to the materials of the collar portion 11, the collar portion 11 may be colored using other methods. For example, it may be configured that the collar portion is colored through a spray coating, screen printing, laser printing, coating, and laminating, after injecting the collar portion other than the pigment. Furthermore, the collar portion 11 may be translucent.

In addition, in the present embodiment, the collar portion 11 is colored differently from the surface color of the outer tube 2 and the surface color of the inner tube 3, however, for example, the collar portion may be colored differently from either one of the color of the outer tube 2 or the color of the inner tube 3. The depth of the color of the outer tube 2, the inner tube 3, and the collar portion 11 is not particularly limited. The color of the collar portion 11 may be configured to be darker than the colors of the outer tube 2 and the inner tube 3, and the color of the collar portion 11 may be configured to be most shallow. As regard the depth of the color of the outer tube 2 and the inner tube 3, one of the tubes may be configured to be darker than the other, or both may be configured to be of the same depth. In the color scheme, a color obtained by combing contrasting density, another color, and translucence may be used.

By adding a color to the collar portion 11, the visibility of the collar portion 11 can be improved, which can improve the discrimination of the collar portion 11 from the outer tube 2, etc. Furthermore, by adding a color to the collar portion 11, the decorative effect can be improved. The color added to the collar portion 11 is not particularly limited, for example, green, blue, and red colors may be added. Generally, green, blue, and red colors easily stand out, and by coloring the collar portion in green, blue, and red colors, the visibility can be improved effectively. Furthermore, the green color gives a sense of reassurance and also has the effect of reducing anxiety, and therefore, by coloring the collar portion 11 in green, a sense of reassurance is imparted to the user, the feeling of anxiety and stress at the time of inserting the tampon are reduced, and the depressing feeling associated with menses can be reduced.

It must be noted that from the viewpoint of securing the strength in the periphery of the hole portion 11a, the diameter of the collar portion 11 is desired to be of a length that is extended by 2 mm towards the outer side than at least the inner diameter of the hole portion. In addition, from the viewpoint of preventing the bodily fluid from adhering to the fingers when the collar portion 11 and the vaginal opening are in contact, the diameter of the collar portion 11 is desired to be at least 15 mm or more.

Furthermore, because the collar portion 11 can be rotated with respect to the grip tube portion 7, when inserting the outer tube 2 inside the body while holding the collar 11, the outer tube 2 can be inserted inside the body while maintaining the appropriate angle, by rotating the collar portion 11 with respect to the outer tube 2. Specifically, the angle and position of the hand holding the tampon applicator 1 change in the state where the push-out opening 8, which is the distal end of the outer tube 2, is in contact with the vaginal opening, and in the state where the outer tube 2 is inserted inside the vagina and the collar portion 11 is in contact with the vaginal opening. At this time, by rotating the collar portion 11 with respect to the outer tube 2, the relative angle between the collar portion 11 and the outer tube 2 can be changed in accordance with the change in the position and angle of the hand with respect to the tampon applicator. Therefore, even when the angle and position of the hand holding the tampon applicator 1 change, the user can smoothly insert the tampon applicator by exerting an appropriate force to the tampon applicator.

Furthermore, the collar portion 11 of the present embodiment is formed by injection-molding a thermoplastic resin using a mold. When injection-molding is performed, the collar portion 11 may be molded together with the outer tube 2, or may be molded separately and then be configured to be fitted through a single-unit forming step during the manufacturing process. Furthermore, the collar portion 11 may be configured in a detachable manner with respect to the outer tube 2, and may also be configured to be fitted by the user before use.

Next, a form of usage of a tampon applicator thus configured is explained. When using the absorber 4, the user inserts the outer tube 2 up to an appropriate position in the vagina. When the outer tube 2 is inserted up to an appropriate position, the flat surface of the back side (outer tube main body side) of the collar portion 11 is arranged near the vaginal opening. Even when an attempt is made to further insert the outer tube 2 in such a state, the collar portion 11 comes in contact with the body of the user. That is, the collar portion 11 exhibits the function of a stopper, and the user can understand that she has been able to insert the outer tube 2 up to the appropriate position. Furthermore, when the outer tube 2 is inserted up to an appropriate position, the collar portion 11 is arranged between the vaginal opening and the fingers, and therefore, soiling of the fingers of the user by the bodily fluid, such as the menstrual blood, can be prevented.

Next, when the user inserts the outer tube 2 up to a predetermined position inside the vagina and then presses the inner tube 3 toward the outer tube 2, the absorber 4 is pushed out from the push-out opening 8 of the outer tube 2, and the absorber 4 is arranged at an appropriate position inside the vagina. In this way, by providing the collar portion 11, the absorber 4 can be easily arranged at the appropriate position without the fingers of the user touching the area near the vaginal opening. By arranging the absorber 4 at the appropriate position, the user feels less discomfort at the time of using the tampon and can use the tampon comfortably.

The entire collar portion 11 functions as the distinguishable display portion 11b, and because the visibility of the collar portion 11 improves, it becomes easy for the user to distinguish the outer tube 2, the inner tube 3, and the collar portion 11. This makes it easy for the user to visually understand the insertion stop position where the collar portion 11 and the vaginal opening come into contact. Because the user can understand that the collar portion 11 and the vaginal opening are in contact, the absorber 4 can be easily arranged at an appropriate position in the vaginal opening. Furthermore, the user can operate the tampon while understanding the position and condition of the collar portion 11. Because the user can understand the operating status, the absorber 4 can be pushed out smoothly and the absorber 4 can be arranged at an appropriate position in the vagina.

Figure 3:
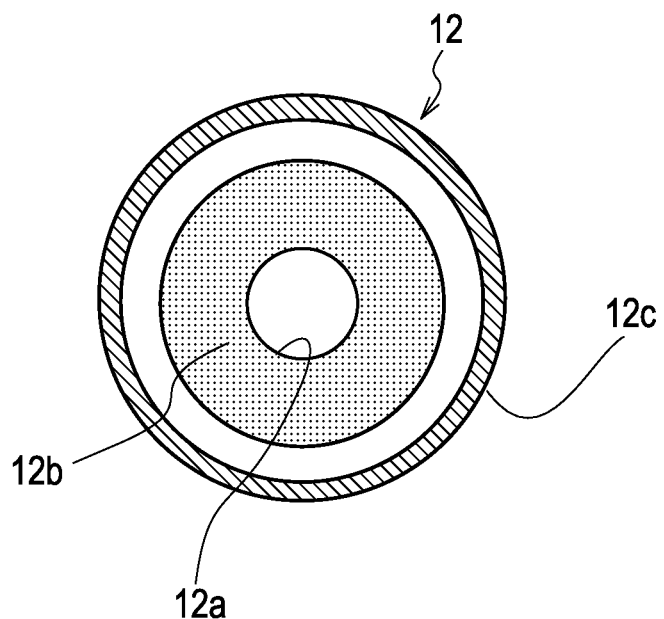
FIG. 3 is a plan view of a collar portion according to a first modification.
Figure 4:
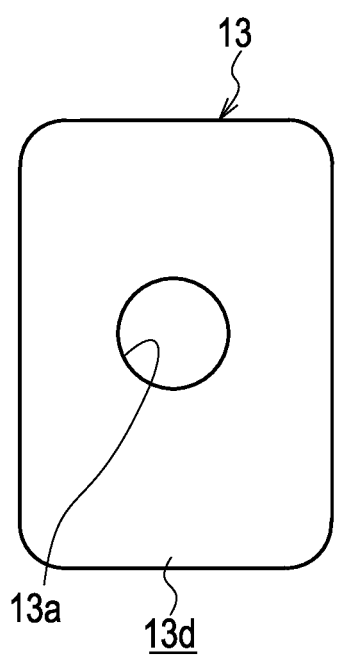
FIG. 4 is a plan view of a collar portion according to a second modification.
Figure 5:
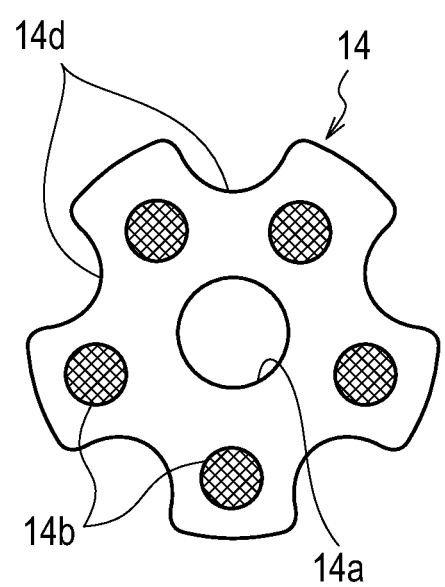
FIG. 5 is a plan view of a collar portion according to a third modification.

It must be noted that the entire collar portion 11 according to the first embodiment is configured as a distinguishable display portion. However, the collar portion 11 according to the present invention is not limited to the present configuration, and a part of the collar portion may be configured as a distinguishable display portion, or a distinguishable friction portion may be provided, or else a distinguishable shape portion may be provided. Next, the collar portion according to a modification will be described. FIG. 3 is a plan view of a collar portion 12 according to a first modification, FIG. 4 is a plan view of a collar portion 13 according to a second modification, and FIG. 5 is a plan view of a collar portion 14 according to a third modification. In the explanation of the modifications provided below, the description of the configuration that is the same as the first embodiment is omitted.

The outer shape of the collar portion 12 according to the first modification is approximately circular in a plan view. A hole portion 12a into which the grip tube portion 7 is inserted is formed in the center of the collar portion 12. The collar distinguishable portion of the collar portion 12 according to the first modification includes a distinguishable display portion 12b and a distinguishable friction portion 12c. The distinguishable display portion 12b is provided in a fixed region that is a periphery of the hole portion 12a and that extends toward the radially outer side from the hole portion 12a. The distinguishable display portion 12b has a dotted pattern. Even when such a distinguishable display portion having a pattern is provided in the collar portion 12, the visibility of the collar portion 12 improves, making it easy for the user to distinguish the collar portion 12 from the outer tube 2, for example. It must be noted that the pattern of the distinguishable display portion is not only dotted, but various configurations, such as a striped pattern, or a pattern having a design such as stars and hearts can be adopted.

The distinguishable friction portion 12c is formed at the radially outer side of the distinguishable display portion 12b. The friction coefficient of the surface of the distinguishable friction portion 12c is different from the friction coefficient of the surface of the outer tube 2 and the inner tube 3. Specifically, an unevenness is formed on the surface of the distinguishable friction portion 12c. The distinguishable friction portion 12c can be formed through mold-injecting, laser molding, thermoforming, applying of hot-melt adhesive, or any other method. Further, the distinguishable friction portion may be configured of rubber, paper, and leather formed at a surface of the collar portion.

Because the distinguishable friction portion 12c is provided in the collar portion 12, the user can distinguish the collar portion 12 and the outer tube, etc., by feeling when the collar portion 12 is touched. Even when the user cannot visually recognize the collar portion 12, the position and condition of the collar portion 12 can be understood. Therefore, the user can understand the operating condition through the collar portion 12, and can smoothly push out the absorber 4 so as to arrange the absorber at an appropriate position inside the vagina. In addition, the user can understand that the collar portion 12 and the vaginal opening are in contact by feeling the vicinity of the vaginal opening. For example, by configuring the friction coefficient of the distinguishable friction portion 12c to be higher than the friction coefficient of the outer tube, etc., the user can recognize that the collar portion and the vaginal opening are in contact by the gritty feeling of the distinguishable friction portion.

The collar portion 12 according to the first modification includes both the distinguishable friction portion and the distinguishable display portion, however, the collar portion 12 may be configured to include either one of the distinguishable friction portion and the distinguishable display portion. The distinguishable friction portion may be provided on the flat surface that is in contact with the vaginal opening, or may be provided in a thickness portion in an outer circumference of the collar portion. Furthermore, the friction coefficient of the surface of the outer tube 2 may be configured to be different from the friction coefficient of the surface of the inner tube 3. According to such a configuration, the user can distinguish the outer tube 2 and the inner tube 3 by the feeling of the hand.

The outer shape of the collar portion 13 according to the second modification is approximately rectangular in a plan view. A hole portion 13a into which the grip tube portion 7 is inserted is formed in the center of the collar portion 13. The collar distinguishable portion according to the second modification is a distinguishable shape portion 13d. The outer peripheral shape of the collar portion 13 is different from the outer peripheral shape of the outer tube 2 and the inner tube 3, and the entire collar portion functions as a distinguishable shape portion 13d.

Due to the feature that the outer peripheral shape of the collar portion 13 is different from the outer peripheral shape of the outer tube 2 and the inner tube 3, the user can distinguish the outer tube 2, etc., from the collar portion 13 by the feeling when the collar portion 13 is touched. Even when the user cannot visually recognize the collar portion 13, the position and condition of the collar portion 13 can be understood. Therefore, the user can understand the operating condition through the collar portion 13, and can smoothly push out the absorber 4 so as to arrange the absorber 4 at an appropriate position inside the vagina.

The collar distinguishable portion of the collar portion 14 according to the third modification includes a shape distinguishable portion and a distinguishable display portion. Five distinguishable display portions 14b are provided on the periphery of the hole portion 14a. In the collar portion 14, a concave portion 14d that caves in towards the hole portion 14a (towards the center) is formed. The concave portion 14d functions as a distinguishable shape portion. By providing the concave portion 14d, the user can recognize the collar portion 14 by the feeling of the concave portion 14d. In addition, the user can arrange the fingers along the concave portion 14d and grip the collar portion 14. Thus, the outer tube 2 can be inserted while placing the fingers in the concave portion 14d, the outer tube is inserted at an appropriate position inside the vagina with an appropriate angle, and the absorber 4 can be easily arranged at an appropriate position inside the vagina. Furthermore, by providing the concave portion 14d, even users with long finger nails and users wearing artificial nails can direct the nails in a direction away from the vaginal opening so that it is possible to prevent the nails from coming in contact with the user's body such as a vaginal opening.

Furthermore, five concave portions 14d are formed and the interval between the concave portions 14d is uniform, and also the five concave portions 14d are arranged to be deviated at an equal angle with respect to the center of the hole portion 14a. By thus providing the collar portion 14, the collar portion 14 can be gripped by five fingers, and the stability at the time of inserting the outer tube 2 can be improved. In addition, by setting a uniform interval between the five concave portions 14d, the collar portion 14 can be gripped by applying a force evenly through the concave portions 14d, and the stability at the time of gripping can be improved. It must be noted that there may be five or more concave portions, or even less than five.

The concave portions 14d may be formed by injection-molding, laser molding, heat molding, and other methods. As regard the shape of the concave portions 14d, various configurations such as streamlined, concave, an isosceles triangle, and a teardrop can be adopted.

Thus, the present invention naturally includes various embodiments, not described herein. Therefore, the technical range of the present invention is to be defined only by the inventive specific matter according to the adequate claims from the above description.

For example, the collar portion may have an outer shape other than a perfect circle in a plan view, and may have a polygon shape such as a rectangle or triangle, a heart shape or a star shape, an elliptical shape, or the shape of the skull of an animal. For example, by shaping the outer shape of the collar portion into a heart shape and the shape of the skull of animals, a medical device like a tampon can be beautified by the collar portion. Thus, the depressing feeling of the user associated with menstruation can be eased, and the willingness for subsequent use can be increased.

Furthermore, the color, the outer peripheral shape, and the friction coefficient of each of the outer tube 2, the inner tube 3, and the collar portion may be configured to be different. As a result of such a configuration, the user can easily recognize each position of the outer tube 2, etc., that configures the tampon applicator. Thus, for example, even a user who is using a tampon for the first time can easily understand each position and the operating method.

Furthermore, the outer circumferential shape of the collar portion is desired to be curved. The curved shape indicates that the configuration may be such that sharp angular portions are not included, and a linear shape may be included partially. By shaping the outer circumference shape of the collar portion in a curved shape, the feeling of holding the collar portion experienced by the user can be mellowed down.

Examples

Hereinafter, distinguishability evaluation of the collar portion according to the present invention will be described in detail with citing examples and comparative examples. The present invention is not limited thereto.
<Visual Distinguishability Evaluation>
(Evaluation Details)

By using a reference collar portion that acted as the reference, and collar portions according to examples 1 through 3 and comparative example 1 that had a different color from the reference collar portion, the distinguishability evaluation was performed with regard to whether or not the reference collar portion and the collar portions according to examples 1 through 3 and comparative example 1 could be visually distinguished.

(Method of Measuring Color Difference)

A 40-mm×25-mm section was taken from the outer tube according to the present embodiment, and set as the reference collar portion. By using the reference collar portion as the color difference-reference color, each collar portion was measured with a measurement device described later, and the color difference (ΔE) of each collar portion from the color difference-reference color was calculated.

(Total Light Transmittance Measurement Device)
  Colorimeter (Konica Minolta CR300)
  Compliant with diffuse illumination/0° viewing angle system of JIS Z 8722
  Measuring head: Φ40 mm
  Light receiving element: silicon photocells (6)
  Light source: Pulsed xenon lamp
  Measurement area: 8 mm
  Standard deviation: Within ΔE*ab 0.07

(Evaluation Method)

By using the collar portions according to examples 1 through 3 and the comparative example 1, it was assessed whether or not a visual distinction from the reference collar portion was possible. The number of monitoring persons was five. Five monitoring persons assessed the distinguishability in each example and comparative example. When a monitoring person assessed that a distinction from the reference collar portion was possible, the collar portion was assessed as being distinguishable, and when a monitoring person assessed that a distinction from the reference collar portion was not possible, the collar portion was assessed as not being distinguishable.

(Evaluation Result)

The evaluation results are shown in Table 1.

TABLE 1

| Configuration of collar unit | | Comp. Example 1 Polyethylene pellet (white) | Example 1 Transparent stopper | Example 2 Colored stopper (white) | Example 3 Colored stopper (green) |
|---|---|---|---|---|---|
| Color difference | ΔL | 3.6 | −47.79 | 7.12 | −15.41 |
| | Δa | −1.11 | 2.65 | −0.17 | −9.48 |
| | Δb | −1.81 | 0.03 | 1.29 | −1.47 |
| | ΔE | 4.17 | 47.86 | 7.23 | 18.15 |
| The no. of those who assessed distinguishable | | 0 | 5 | 1 | 5 |

The collar portions according to examples 1 through 3 had a color difference of 7.3 or more with respect to the reference collar portion, and were assessed as being distinguishable by at least one monitoring person. Therefore, it was concluded that a collar portion was visually distinguishable because the color difference between the outer tube or the inner tube and the collar portion was 7.3 or more. Furthermore, the collar portion according to example 1 and example 3 was assessed as being distinguishable by all of the five monitoring persons.

Therefore, the more appropriate color difference between the outer tube or the inner tube and the collar portion is desired to be 19 or more.

<Distinguishability Evaluation Based on Touch>

(Evaluation Details)

By using an outer tube, and collar portions according to examples 1 through 9 and comparative examples 1 through 6 that had a different friction coefficient from the outer tube, the distinguishability evaluation was performed with regard to whether or not the collar portions according to examples 1 through 9 and comparative examples 1 through 6 and the outer tube could be distinguished by touch.

(Method of Measuring the Friction Coefficient)

The surface of the collar portions according to examples 1 through 9 and comparative examples 1 through 6 that was in contact with the vaginal opening was mounted on a block as the surface to be measured. The block is 100 mm×50 mm. The diameter of the collar portion is 32 mm and the inner diameter of the hole portion is 9.9 mm. In order that the center of the hole portion of the collar portion matched the center of the block, the collar portion was joined with the block through two 7-mm×10-mm double-sided tapes. The block was arranged on the glass plate of a measurement device described later, a slip tester was inclined at a constant speed, and the angle (θ) of inclination at the time the block started to slip, and the time (t) required until the block slipped 50 mm from the time of starting inclination were measured.

The coefficient of static friction and the coefficient of dynamic friction were calculated based on the angle (θ) of inclination and the time (t) required for inclination.

Coefficient of static friction: tan θ
  Coefficient of dynamic friction: tan θ (1-2*5/980.7t)

(Total Light Transmittance Measurement Device)
  Slip tester (Yasuda Seiki Seisakusho, Ltd. Model: 162-SLM)
  Speed (1° per approx. 1 sec., 60° per 1 min.)
  Glass plate dimensions: 485 mm×124 mm×3 mm
  Motor: AC100 V, 10 W reversible motor
  Power supply: AC100 V, 60 HZ
  Block (100 mm×50 mm, 500 g)
  Double-sided tape (7 mm×10 mm, 3M Company, Scotch)

(Evaluation Method)

By using the collar portions according to examples 1 through 9 and comparative examples 1 through 6, it was assessed whether or not the outer tube and the collar portion could be distinguished by the feeling of the hand. The number of monitoring persons was five. Five monitoring persons assessed the distinguishability in each example and comparative example. When a monitoring person assessed that a distinction from the reference collar portion was possible, the collar portion was assessed as being distinguishable, and when a monitoring person assessed that a distinction from the collar portion was not possible, the collar portion was assessed as not being distinguishable.

(Evaluation Result)

The evaluation results are shown in Table 2.

TABLE 2

| | Example 1 | Example 2 | Example 3 | Example 4 | Example 5 | Example 6 | Example 7 | Example 8 |
|---|---|---|---|---|---|---|---|---|
| Indination angle θ (°) | 16 | 20 | 17 | 23 | 22 | 23 | 23 | 22 |
| Indination angle θ (Radian) | 0.27925266 | 0.34906585 | 0.296705973 | 0.401425728 | 0.383972435 | 0.401425728 | 0.401425728 | 0.363972435 |
| Time (sec) | 9.95 | 9.59 | 7.15 | 6.81 | 4.86 | 5.75 | 7.08 | 6.22 |

TABLE 2-continued

|  | | | | | | | | |
|---|---|---|---|---|---|---|---|---|
| Coefficient of static friction | 0.286745386 | 0.363970234 | 0.305730681 | 0.424474616 | 0.404026226 | 0.424474816 | 0.424474818 | 0.404026226 |
| Coefficient of dynamic friction | 0.257652732 | 0.32637857 | 0.283440742 | 0.394999202 | 0.384004125 | 0.399587183 | 0.393830565 | 0.398401232 |
| The no. of those who assessed distinguishable | 5 | 5 | 5 | 5 | 5 | 5 | 5 | 5 |

|  | Example 9 | Comp. Example 1 | Comp. Example 2 | Comp. Example 3 | Comp. Example 4 | Comp. Example 5 | Comp. Example 6 |
|---|---|---|---|---|---|---|---|
| Indination angle θ (°) | 23 | 13 | 14 | 14 | 14 | 15 | 14 |
| Indination angle θ (Radian) | 0.401425728 | 0.226892803 | 0.244346095 | 0.244346095 | 0.244346095 | 0.261799386 | 0.244346095 |
| Time (sec) | 7.36 | 3.97 | 3.89 | 5.39 | 3.09 | 7.86 | 5.08 |
| Coefficient of static friction | 0.424474816 | 0.238868191 | 0.249328002 | 0.249328003 | 0.249328003 | 0.267949192 | 0.249328003 |
| Coefficient of dynamic friction | 0.392618646 | 0.221522349 | 0.239438272 | 0.235624751 | 0.241497573 | 0.246473913 | 0.236412878 |
| The no. of those who assessed distinguishable | 5 | 0 | 0 | 0 | 0 | 0 | 0 |

The five monitoring persons assessed each of the collar portions according to examples 1 through 9 to be distinguishable, and it was thus concluded that the collar portions could be distinguished by touch. On the other hand, the five monitoring persons assessed each of the collar portions according to comparative examples 1 through 6 to be indistinguishable. Among the examples, example 1 had the smallest coefficient of static friction and the smallest coefficient of dynamic friction, and it was concluded that if the friction coefficient was larger than that in example 1, the collar portion could be distinguished by touch. That is, a collar portion having a coefficient of static friction of 0.286745386 or more, and a coefficient of dynamic friction of 0.257652732 or more could be used preferably.

In addition, the entire content of Japanese Patent Application No. 2011-044144 (filed on Mar. 1, 2011) is incorporated in the present specification by reference.

INDUSTRIAL APPLICABILITY

Due to the feature that a collar distinguishable portion having at least any one of the distinguishable display portion, the distinguishable friction portion, and the distinguishable shape portion is provided in the collar portion of the applicator for the tampon according to the present invention, the user can easily distinguish between the outer tube and inner tube, and the collar portion. Thus, the user can clearly understand by eyes and by feel that the collar portion is in contact with the vaginal opening, which enables the user to easily arrange the absorber at an appropriate position inside the vagina.

The invention claimed is:

1. A tampon applicator, comprising:
an outer tube including an absorber therein, the outer tube having:
a push-out opening at one side from which the absorber is configured to be pushed out, and
a grip tube portion at the other side;
an inner tube inserted into the grip tube portion and configured to move further into the outer tube to push out the absorber outward from the push-out opening, and
a collar portion protruding outwardly in a radial direction from an outer circumference surface of the grip tube portion of the outer tube,
wherein
the collar portion includes a distinguishable friction portion having a friction coefficient different from a friction coefficient of a surface of at least either one of the outer tube and the inner tube, and
the distinguishable friction portion is provided only on an outer periphery of the collar portion.

2. A tampon applicator, comprising:
an outer tube including an absorber therein, the outer tube having:
a push-out opening at one side from which the absorber is configured to be pushed out, and
a grip tube portion at the other side;
an inner tube inserted into the grip tube portion and configured to move further into the outer tube to push out the absorber outward from the push-out opening, and
a collar portion protruding outwardly in a radial direction from an outer circumference surface of the grip tube portion of the outer tube,
wherein
the collar portion includes a distinguishable friction portion having a friction coefficient different from a friction coefficient of a surface of at least either one of the outer tube and the inner tube,
the collar portion further comprises a distinguishable display portion having a color different from at least either one of the outer tube and the inner tube,
the distinguishable friction portion is formed only on an outer periphery of the collar portion, and
the distinguishable display portion is formed on an inner periphery of the collar portion and extends toward the outer periphery in the radial direction.

3. A tampon applicator, comprising:
an outer tube including an absorber therein, the outer tube having:
a push-out opening at one side from which the absorber is configured to be pushed out, and a grip tube portion at the other side;

an inner tube inserted into the grip tube portion and configured to move further into the outer tube to push out the absorber outward from the push-out opening; and a collar portion protruding outwardly in a radial direction from an outer circumference surface of the grip tube portion of the outer tube, wherein the collar portion includes a distinguishable shape portion, and the distinguishable shape portion has a plurality of concave portions on an outer periphery of the collar portion and extending toward a center of the collar portion.

4. The tampon application according to claim 3, wherein the collar portion further includes a plurality of distinguishable display portions having a color different from at least either one of the outer tube and the inner tube.

5. The tampon application according to claim 4, wherein the plurality of distinguishable display portions and the plurality of concave portions are alternatingly arranged in a circumferential direction of the collar portion.

* * * * *